(12) United States Patent
Ranucci et al.

(10) Patent No.: US 11,378,508 B2
(45) Date of Patent: Jul. 5, 2022

(54) MEASURING DEVICE FOR VISCOMETRIC ANALYSIS ON A BIOLOGICAL FLUID

(71) Applicant: VISCOP S.R.L., Rome (IT)

(72) Inventors: Marco Ranucci, Rome (IT); Francesco Napolitano, Rome (IT); Franco Scorziello, Rome (IT)

(73) Assignee: Viscop S.r.l., Rome (IT)

( * ) Notice: Subject to any disclaimer, the term of this patent is extended or adjusted under 35 U.S.C. 154(b) by 6 days.

(21) Appl. No.: 16/331,126

(22) PCT Filed: Sep. 6, 2017

(86) PCT No.: PCT/IB2017/055359
§ 371 (c)(1),
(2) Date: Mar. 6, 2019

(87) PCT Pub. No.: WO2018/047070
PCT Pub. Date: Mar. 15, 2018

(65) Prior Publication Data
US 2019/0212240 A1    Jul. 11, 2019

(30) Foreign Application Priority Data

Sep. 6, 2016 (IT) .......................... 102016000090231

(51) Int. Cl.
*G01N 11/14* (2006.01)
*G01N 33/49* (2006.01)

(52) U.S. Cl.
CPC ....... *G01N 11/142* (2013.01); *G01N 33/4905* (2013.01)

(58) Field of Classification Search
CPC .......................... G01N 11/142; G01N 33/4905
(Continued)

(56) References Cited

U.S. PATENT DOCUMENTS 5,181,415 A * 1/1993 Esvan .................... G01N 11/14
436/69

FOREIGN PATENT DOCUMENTS

CN    202770732 U    3/2013
JP    S61149841 A    7/1986
(Continued)

OTHER PUBLICATIONS

A translation of the JP H61-149841 reference (Year: 2021).*

*Primary Examiner* — John Fitzgerald
*Assistant Examiner* — Rodney T Frank
(74) *Attorney, Agent, or Firm* — David B. Tingey; Bryant J. Keller; Kirton McConkie

(57) ABSTRACT

The measuring device for viscometric analysis on a biological fluid, comprises a base frame and a support element associated with the base frame, having an elongated shape and with: a first ending part associable with motor means to set in rotation the support element around an axis of rotation (A); a second ending part opposite to the first ending pan and positionable in contact with a fluid to be analyzed contained in a collecting vessel; sensor means adapted to measure the viscosity values of the fluid; wherein the sensor means comprise a first sensor element and a second sensor element associated with the support element and operable in rotation around the axis of rotation (A) at a predefined rotational speed, and operatively connected to optical means adapted to detect a speed change between the sensor means depending on said viscosity values.

12 Claims, 1 Drawing Sheet

(58) Field of Classification Search
USPC .......................................................... 73/54.28
See application file for complete search history.

(56) References Cited

FOREIGN PATENT DOCUMENTS

| | | |
|---|---|---|
| JP | H04346056 A | 12/1992 |
| JP | H11311594 A | 11/1999 |

* cited by examiner

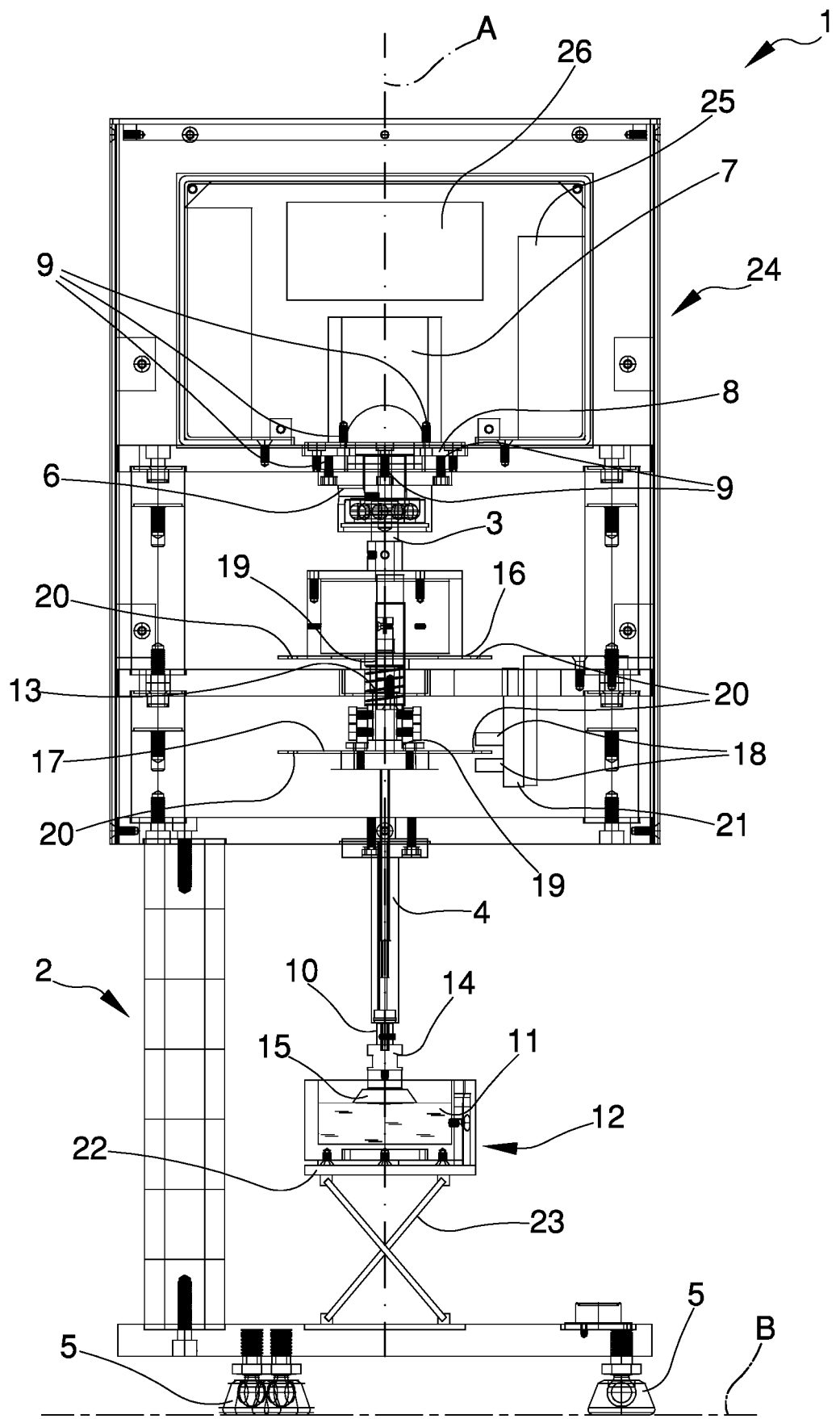

MEASURING DEVICE FOR VISCOMETRIC ANALYSIS ON A BIOLOGICAL FLUID

TECHNICAL FIELD

The present invention relates to a measuring device for viscometric analysis on a biological fluid, particularly blood or plasma.

BACKGROUND ART

For some time now, in the medical field, diagnostic studies have been carried out on the viscoelastic characteristics of blood, and in particular on the relative variations during the coagulative phase of the hemostatic proces.

Coagulation velocity and clotting stability of a blood sample depend on multiple factors related to the patient's clinical picture and directly connected to the activity of the coagulation system, platelet function, fibrinolysis, and a variety of other factors influenced by genetic factors, illnesses, and drug intake.

To date, the measurement of the viscosity and elasticity of the clot occurs using several methods which explore hemodynamic processes during the coagulative phase.

Generally, such methods require the addition of agents to stimulate the hemostatic-coagulative process such as, e.g., kaolin, tissue factor, and others. Nevertheless, in this case, the hemostatic-coagulative process is measured at static conditions, in this specific instance the blood sample is made to rotate at a shear speed value, i.e. shear rate, which does not correspond to a shear rate value existing physiologically in any point of body circulation.

In detail, a first known method is the so-called thromboelastography (TEG). Thromboelastography envisages a blood sample taken from the patient being transferred to a vessel made to rotate and containing inside it sensor means which are adapted to detect variations in blood resistance and elasticity.

In the absence of activation factors (native TEG) the process occurs in extremely long times, pre-venting its implementation in clinical practice.

For this reason, the blood sample is activated by means of kaolin, or alternatively by the combination of kaolin with tissue factor (rapid-TEG).

The sensor means are operatively connected to processing means to process the viscosity values detected in graphic representations that vary according to the specific requirements of industry operators.

In particular, the blood sample is made to rotate at a preset shear rate value, i.e. shear rate, substantially equal to 0.5 $sec^{-1}$; this value is unlikely to correspond to the corresponding physiological shear rate which the blood undergoes in the blood vessels, thus decreasing the truthfulness of the analysis.

Furthermore, this first method has a number of drawbacks among which the fact that they provide arbitrary units of measurement such as e g millimeters, which are not comparable to experimental viscosity data expressed in Poiseuille according to the International System and are therefore unlikely to be true.

An alternative method is the so-called ReoRox wherein the vessel containing the blood sample undergoes free oscillation and the sensor means separately detect variations in the elasticity and viscosity of the sample itself.

In the case of the above method, the shear rate value undergone by the blood is substantially equal to 0.5 $sec^{-1}$ which, although likely similar to the physiological values of the blood with respect to the previous methods, is preset and unchangeable.

In this case too, the units of measurement whereby the detected data are expressed and represented in the graph are arbitrary and do not permit direct comparison with other experimental viscosity data.

A second known method is the so-called thromboelastometry (ROTEM).

Similarly to thromboelastography (TEG), thromboelastometry (ROTEM) also provides for the blood sample to be contained inside a vessel having sensor means operatively linked to means of processing the detected data. Like thromboelastography, several activators are envisaged such as kaolin for the INTEM method, or tissue factor for the EXTEM method.

In this case, the sensor means are made to rotate until they are slowed down by blood coagulation.

The data are therefore detected according to the slow-down in the rotation of the sensor means according to the formation of the clot. The processing means read and process this slowdown and translate it graphically into a curve.

Nevertheless, in this case too, thromboelastometry (ROTEM) measures the variations in elasticity and resistance of the clot during the hemostatic phase, providing data expressed in millimeters and therefore not comparable to experimental viscosity measurements.

Furthermore, the presence of artificial activators produces a burst of thrombin which causes platelet activation regardless of the presence of platelet inhibiting drugs such as, e.g., aspirin, thienopyridine, ticagrelor, widely used in clinical practice.

To overcome the above drawback complex TEG thromboelastograph techniques are needed which are laborious to achieve (platelet mapping).

DESCRIPTION OF THE INVENTION

The main aim of the present invention is to provide a measuring device for viscosimetric analysis on a biological fluid that permits measurements expressed in units of measurement directly comparable to the experimental viscosity data.

One object of the present invention is to provide a measuring device for viscosimetric analysis on a biological fluid that permits exploring the coagulative hemostatic process in a dynamic way and in continuous mode. Another object of the present invention is to provide a measuring device for viscosimetric analysis on a biological fluid that simulates the physiological activation of the blood, avoiding the use of activators and thus also permitting an assessment of the platelet function.

A further object of the present invention is to provide a measuring device for viscosimetric analysis on a biological fluid which allows to overcome the aforementioned drawbacks of the prior art within the ambit of a simple, rational, easy, efficient to use and cost-effective solution.

The aforementioned objects are achieved by the present measuring device for viscosimetric analysis on a biological fluid having the characteristics of claim 1.

BRIEF DESCRIPTION OF THE DRAWINGS

Other characteristics and advantages of the present invention will become more evident from the description of a preferred, but not exclusive, embodiment of a measuring device for viscosimetric analysis on a biological fluid, illustrated by way of an indicative, but non-limiting example, in the attached drawings in which:

FIG. 1 is a sectional view of the device according to the invention.

EMBODIMENTS OF THE INVENTION

With particular reference to these illustrations, reference numeral 1 globally indicates a measuring device for viscosimetric analysis on a biological fluid.

The device 1 comprises a base frame 2 and a support element (e.g., a first portion of the support element 3 and a second portion of the support element 4) associated with the base frame 2.

The base frame 2 is provided with holding elements 5 to a substantially horizontal flat surface B.

The holding elements 5 permit regulating the height and therefore positioning the device levelled with respect to the flat surface B.

The support element (e.g., the first portion 3 and the second portion 4) has an elongated shape and is provided with a first ending part 6 associable with motor means 7 to set in rotation the support element (e.g., the first portion 3 and the second portion 4) around an axis of rotation A.

With reference to the particular embodiment shown in the illustrations, the first ending part 6 is a flange provided with holes for boltin.

The flange 6 is coupleable with a corresponding flanged plate 8 with which the motor means 7 are provided.

The flange 6 and the flanged plate 8 are associable the one with the other by interposition of connecting elements 9 of the type of screws or bolts.

Furthermore, the support element (e.g., the first portion 3 and the second portion 4) is provided with a second ending part 10 opposite to the first ending part 6 connected to a contact element (e.g., the fastening portion 14 and/or the contact portion 15 of the contact element) and positionable in contact with a biological fluid 11 to be analyzed contained in a collecting vessel 12.

Within the scope of the present treatise by the expression "biological fluid" reference is made to the blood taken from a patient and in coagulation phase.

The collecting vessel 12 contains a heating/cooling element and a temperature sensor for the feedback control of the temperature of the vessel itself; such element allows varying the work temperature at which the viscosity values of the fluid 11 are detected depending on the specific users needs.

The device 1 comprises a holding base 22 of the collecting vessel 12 associated with the base frame 2 and adjustment means 23 for adjusting the height of the holding base 22.

The adjustment means 23 permit varying the height at which the collecting vessel 12 is positioned according to the dimensions of the latter and to the quantity of fluid 11 contained therein.

The support element (e.g., the first portion 3 and the second portion 4) comprises the first portion 3 associable with the motor means 7 and the second portion 4 in sliding contact with the fluid 1.

The first portion 3 and the second portion 4 are associated with one another by interposition of motion transmission means 13 from the first portion 3 to the second portion 4.

Preferably, the second portion 4 comprises the contact element (e.g., the fastening portion 14 and/or the contact portion 15) positionable in contact with the fluid 1.

As can be seen in the illustrations, the contact element (e.g., the fastening portion 14 and/or the contact portion 15) has the fastening portion 14 associated with the second ending part 10 and the contact portion 15 with a substantially truncated-cone shape having the base arranged in sliding contact with the fluid 11.

Depending on the measuring method, the contact element (e.g., the fastening portion 14 and/or the contact portion 15) can be placed in contact with the bottom of the vessel 12 by means of the adjustment of its positioning using the adjustment means 23.

The device 1 comprises sensor means 16, 17 adapted to measure the viscosity values of the fluid 11.

According to the invention, the sensor means 16, 17 comprise a first sensor element 16 and a second sensor element 17 associated with the support element (e.g., the first portion 3 and the second portion 4) and operable in rotation around the axis of rotation A at a predefined rotational speed, and operatively connected to optical means 18 adapted to detect a speed change depending on the viscosity values.

In other words, the optical means 18 are adapted to detect the characteristics of the rotation which differ from one another depending on the fluid viscosity values.

It is worth to underline that the predefined rotational speed can be set by the user depending on the specific analysis requirements.

Preferably, the predefined rotational speed is substantially equal to 50 min-t.

The first sensor element 16 and the second sensor element 17 comprise a first disc element and a second disc element, respectively.

With reference to the particular embodiment shown in the illustrations, the first disc element 16 is associated with the first portion 3 and the second disc element 17 is associated with the second portion 4.

Preferably, the disc elements 16, 17 are mutually coaxial.

Advantageously, the disc elements 16, 17 are made of opaque materia.

The disc elements 16, 17 are associated with the support element (e.g., the first portion 3 and the second portion 4) by interposition of connection means 19.

The connection means 19 comprise a flanged bearing of the type known to the expert in the sector.

In detail, the first portion 3 supports in rotation the first disc element 16.

The second portion 4 is driven and the rotary motion is transmitted to the latter by means of the motion transmission means 13.

The motion transmission means 13 comprise an elastic element.

Advantageously, the motion transmission means 13 (e.g., an elastic element) is the type of a spiral spring.

The motion transmission means 13 (e.g., a spiral spring) in the absence of external stresses in the direction opposite to that of rotation of the axis of rotation A, takes on a rigid-body shape adapted to transmit the rotary motion, at the predefined rotation speed, from the first portion 3 to the second portion 4.

On the contrary, in the presence of external stresses in the direction opposite to that of rotation of the axis of rotation A, the deformation of the motion transmission means 13 (e.g., the spiral spring) permits differing the rotation speed of the first disc element 16 and of the second disc element 17, the latter rotating out-of-phase with respect to the first disc element 16, proportional to the viscosity of the fluid 11.

The disc elements 16, 17 are operable in rotation around the axis of rotation A between:

a first operating configuration in which the disc elements 16, 17 rotate in-phase at the predefined speed which is transmitted by the motion transmission means 13 (e.g., an elastic element), i.e. by the spiral spring, from the first portion 3 to the second portion 4; and a second operating configuration in which the first disc element 16 and the second disc element 17 rotate out-of-phase to each other.

Advantageously, the first disc element 16 and the second disc element 17 respectively comprise at least one slot 20.

With reference to the particular embodiment shown in the illustrations, the first disc element 16 and the second disc element 17 comprise two slots 20 made on diametrically opposite portions of the disc elements themselves.

In the first operating configuration, the slots 20 are substantially aligned to each other, and in the second operating configuration the slots 20 define a phase delay detected by the optical means 18.

The phase delay depends on the shearing force acted by the fluid 11 on the contact portion 15.

In particular, the optical means 18 are adapted to detect the passage of each slot 20 depending on the viscosity values.

More in detail, the optical means 18 are adapted to determine the phase difference between the disc elements 16, 17.

Preferably, the optical means 18 are associated with the base frame 2 by interposition of a support arm 21.

In a preferred embodiment, the optical means 18 comprise a first optical unit arranged behind the connection means 19 and not visible in detail in the illustration, and a second optical unit aligned with the second disc element 17. The device 1 is operatively connected to acquisition and processing means 26 to process the viscosity values depending on the phase delay.

Within the scope of the present treatise by acquisition and processing means 26 is meant a computer, schematically shown in the illustration by a rectangle, provided with data control and processing software, adapted to process and integrate the rotation speed of the disc elements 16, 17 and the relative conversion in viscosity values expressed in poise and analogous multiples and sub-multiples.

Preferably, the device 1 is operatively connected to remote processing means to process the viscosity values leaving the acquisition and processing means 26. Advantageously, the link between the acquisition and processing means 26 and the device 1 is made through interface means.

With reference to the particular embodiment shown in the illustrations, the device 1 comprises temperature control means for controlling the temperature of the fluid 11, not shown in the illustrations.

Furthermore, the device 1 comprises protection means 24 for protecting the optical means 18 and the disc elements 16, 17.

The protection means 24 are associated with the base frame 2.

Preferably, the protection means 24 comprise a box-shaped element 25 which accommodates the motor means 7 and in which the support element (e.g., the first portion 3 and the second portion 4) is at least partly contained.

With reference to the particular embodiment shown in the illustrations, the box-shaped element 25 houses the computer 26.

The contact portion 15 is arranged externally to the protection means 24.

Before the detailed explanation of the operation of the present invention and its particular structural aspects, it is useful to point out that the fact of envisaging the application of a rotation speed, i.e., of a physiological shear rate between 50 and 100 $min^{-1}$, exactly the same as that found, e.g., at coronary circulation or that of the arterioles, takes on particular clinical importance, in the light of the fact that in such district the coagulative hemostatic phenomena take on great importance both as regards the genesis of thrombosis and the interruption of bleeding.

The operation of the present invention is as follows.

The collecting vessel 12 is positioned on the holding base 22, the latter is moved by means of the height adjustment means 23 in such a way that the contact element (e.g., the fastening portion 14 and/or the contact portion 15) is in the suitable position for the measurement.

The first portion 3 and the second portion 4 are therefore operated in rotation around the axis of rotation A.

During the first operating configuration, the disc elements 16, 17 rotate and the slots 20 are aligned with one another. In other words, the disc elements 16, 17 and the relative slots 20 rotate in phase.

The predefined rotational speed is transmitted from the first portion 3 to the second portion 4 through the motion transmission means 13 (e.g., an elastic element).

With the variation of the viscosity values of the fluid 11, i.e., during the coagulation of the blood, the second disc element 17 undergoes a change in speed due to the shear force applied by the fluid 11 on the contact element (e.g., the fastening portion 14 and/or the contact portion 15).

In detail, the variations in the viscosity of the fluid 11 determine a shear force that counteracts the rotation of the second portion 4 and, therefore, of the contact portion 15.

In fact, during the second operating phase the disc elements 16, 17 rotate out-of-phase the one to the other and, in the case in question, the second disc element 17 rotates at a rotation speed correlated with the shear force applied on the contact portion 15 by the fluid 11.

More in detail, the optical means 18 detect the phase delay by means of the passage of the slots 20.

At the same time, the rotation speeds are processed by the acquisition and processing means adapted to provide the density values of the fluid 11.

It has in practice been ascertained that the described invention achieves the intended objects.

It is underlined that the particular solution of providing rotating disc elements together with the presence of a contact element adapted to contact the surface of the fluid permits taking measurements expressed in units of measurement directly comparable with experimental viscosity data, exploring the coagulative hemostatic process in a dynamic way and in continuous mode.

The invention claimed is:

1. A measuring device for viscometric analysis on a biological fluid, particularly blood or plasma, which biological fluid comprises blood or plasma taken from a patient and that is in a coagulation phase, said measuring device comprising a base frame and at least one support element associated with said base frame, having an elongated shape and comprising a first portion and a second portion connected with one another by interposition of motion transmission means from said first portion to said second portion and respectively provided with:

a first ending part associable with motor means to set in rotation said support element around an axis of rotation;

a second ending part opposite to said first ending part connected to a contact element configured to slide across an upper surface of the biological fluid to be analyzed contained in a collecting vessel; and sensor means adapted to measure viscosity values of said biological fluid comprising:

at least a first sensor element comprising a first disc element and at least a second sensor element comprising a second disc element and associated with said support element and operable in rotation around said axis of rotation at a predefined rotational speed, and operatively connected to optical means adapted to detect a speed change between said sensor means depending on said viscosity values, said first disc element being connected with said first portion and said second disc element being connected with said second portion, wherein said motion transmission means comprise at least one elastic element and said optical means are adapted to detect an angular speed and a phase of rotation of said disc elements, and wherein said predefined rotational speed is comprised between 50 and 100 $min^{-1}$ so as to mimic circulation in arterioles where the biological fluid to be analyzed lacks an artificial activator so as to permit assessment of platelet function in the biological fluid.

2. The device according to claim 1, wherein said disc elements are mutually coaxial.

3. The device according to claim 1, wherein said first disc element and said second disc element respectively comprise at least one slot, said optical means being adapted to detect a passage of said slot depending on said viscosity values.

4. The device according to claim 1, wherein said disc elements are operable in rotation around said axis of rotation between:

a first operating configuration in which said disc elements rotate in-phase at said predefined speed which is transmitted by said elastic element from said first portion to said second portion; and a second operating configuration in which said first disc element and said second disc element rotate out-of-phase to each other, a phase shift of said disc elements being proportional to said viscosity values.

5. The device according to claim 4, wherein said first operating configuration said slots are substantially aligned to each other, and in said second operating configuration said slots define a phase delay detected by said optical means, said phase delay depending on a shearing force acted by said fluid on said contact portion.

6. The device according to claim 1, further comprising a holding base of said collecting vessel associated with said base frame and adjustment means for adjusting a height of said holding base.

7. The device according to claim 1, further comprising protection means for protecting said optical means and said disc elements, said protection means being associated with said base frame.

8. The device according to claim 7, wherein said protection means comprise at least one box-shaped element which accommodates said motor means and acquisition and processing means of said viscosity values and in which said support element is at least partly contained, said contact element being arranged externally to said box-shaped element.

9. The device according to claim 8, wherein said measuring device is operatively connected to remote processing means to process said viscosity values leaving said acquisition and processing means.

10. A measuring device for viscometric analysis on a biological fluid, comprising at least one of blood and plasma that is taken from a patient and that is in a coagulation phase, said measuring device comprising a base frame and at least one support element associated with said base frame, having an elongated shape and comprising a first portion and a second portion connected with one another by interposition of motion transmission means from said first portion to said second portion and respectively provided with: a first ending part associable with motor means to set in rotation said support element around an axis of rotation; a second ending part opposite to said first ending part and connected to a contact element configured to slide across an upper surface of the biological fluid to be analyzed, which is contained in a collecting vessel; and sensor means adapted to measure at least one viscosity value of said biological fluid comprising: at least a first sensor element comprising a first disc element and at least a second sensor element comprising a second disc element and associated with said support element and operable in rotation around said axis of rotation at a predefined rotational speed, and operatively connected to optical means adapted to detect a speed change between said sensor means depending on said at least one viscosity value, said first disc element being connected with said first portion and said second disc element being connected with said second portion, wherein said motion transmission means comprise at least one elastic element and said optical means are adapted to detect an angular speed and a phase of rotation of said disc elements, wherein said predefined rotational speed is comprised between 50 and 100 $min^{-1}$ so as to mimic circulation in arterioles where the biological fluid lacks an artificial activator so as to permit assessment of platelet function in the biological fluid, wherein said measuring device is operative and wherein said disc elements are operable in rotation around said axis of rotation between: a first operating configuration in which said disc elements rotate in-phase at said predefined speed which is transmitted by said elastic element from said first portion to said second portion; and a second operating configuration in which said first disc element and said second disc element rotate out-of-phase to each other, with a phase shift of said disc elements being proportional to said at least one viscosity value.

11. The device according to claim 10, wherein the measuring device comprises a collecting vessel that comprises the biological fluid, and wherein the biological fluid lacks the artificial activator.

12. A measuring device for viscometric analysis on a biological fluid, particularly blood or plasma, which biological fluid comprises blood or plasma taken from a patient and that is in a coagulation phase, said measuring device comprising a base frame and at least one support element associated with said base frame, having an elongated shape and comprising a first portion and a second portion connected with one another by interposition of motion transmission means from said first portion to said second portion and respectively provided with:

a first ending part associable with motor means to set in rotation said support element around an axis of rotation;

a second ending part opposite to said first ending part connected to a contact element and configured to slide across an upper surface of the biological fluid to be analyzed, which is contained in a collecting vessel;

sensor means adapted to measure viscosity values of said fluid comprising:

at least a first sensor element comprising a first disc element and at least a second sensor element comprising a second disc element and associated with said support element and operable in rotation around said axis of rotation at a predefined rotational speed, and operatively connected to optical means adapted to detect a speed change between said sensor means depending on said viscosity values, said first disc element being connected with said first portion and said second disc element being connected with said second portion, wherein said motion transmission means comprise at least one elastic element and said optical means are adapted to detect an angular speed and a phase of rotation of said disc elements, and wherein said predefined rotational speed is comprised between 50 and 100 $\text{min}^{-1}$ so as to mimic circulation in arterioles where the biological fluid to be analyzed lacks an artificial activator so as to permit assessment of platelet function in the biological fluid; and temperature control means for controlling the temperature of said fluid wherein said collecting vessel comprises a heating/cooling element and a temperature sensor for feedback control of the temperature of said fluid.

* * * * *